(12) United States Patent
Hagen et al.

(10) Patent No.: US 10,451,550 B2
(45) Date of Patent: Oct. 22, 2019

(54) METHODS AND DEVICES EMPLOYING THERMOPLASTICS FROM THE POLYARYLETHERKETONE (PAEK) FAMILY OF SEMI-CRYSTALLINE THERMOPLASTICS FOR CALIBRATION AND/OR MONITORING OF OPTICAL MEASUREMENT DEVICES

(71) Applicant: Gen-Probe Incorporated, San Diego, CA (US)

(72) Inventors: Norbert D. Hagen, Carlsbad, CA (US); David Opalsky, San Diego, CA (US); George T. Walker, San Diego, CA (US); Byron J. Knight, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 366 days.

(21) Appl. No.: 15/176,861

(22) Filed: Jun. 8, 2016

(65) Prior Publication Data

US 2016/0363532 A1 Dec. 15, 2016

Related U.S. Application Data

(60) Provisional application No. 62/173,045, filed on Jun. 9, 2015.

(51) Int. Cl.
*G01N 21/64* (2006.01)
*G01N 21/27* (2006.01)

(52) U.S. Cl.
CPC ........... *G01N 21/64* (2013.01); *G01N 21/276* (2013.01); *G01N 21/645* (2013.01)

(58) Field of Classification Search
CPC ..... G01N 21/64; G01N 21/276; G01N 21/645
(Continued)

(56) References Cited

U.S. PATENT DOCUMENTS

2008/0316483 A1\* 12/2008 Tai .................. G01N 21/35
356/326
2011/0148764 A1 6/2011 Gao
(Continued)

FOREIGN PATENT DOCUMENTS

EP 1950554 A1 7/2008
EP 2787351 A1 10/2014

OTHER PUBLICATIONS

USPTO, Non-Final Office Action, U.S. Appl. No. 15/176,867, dated Mar. 23, 2018.
(Continued)

*Primary Examiner* — David P Porta
*Assistant Examiner* — Gisselle M Gutierrez
(74) *Attorney, Agent, or Firm* — Sterne, Kessler, Goldstein & Fox P.L.L.C.; Charles B. Cappellari

(57) ABSTRACT

Optical reference devices for calibrating or monitoring the performance of an optical measurement device, such as a fluorometer, are made from thermoplastics from the polyaryletherketone (PAEK) family of semi-crystalline thermoplastics, including polyether ether ketone (PEEK). The reference device may be made as a master reference device having a known emission output—as determined by a standard optical measurement device—that is used to calibrate other optical measurement devices against the standard. The reference device may be made in the shape of a receptacle vial so that the reference device can be placed in the receptacle holding structure of an instrument in which the optical measurement device is installed and used to calibrate or monitor the optical measurement device within the instrument. The reference device may be part of the probe of a pipettor or pick and place mechanism or it may be a cap that can be secured to the end of such a probe.

14 Claims, 12 Drawing Sheets

(58) Field of Classification Search
USPC .................................................... 250/252.1
See application file for complete search history.

(56) References Cited

U.S. PATENT DOCUMENTS

| | | |
|---|---|---|
| 2011/0160073 A1 | 6/2011 | Kordunsky et al. |
| 2012/0053434 A1 | 3/2012 | Saito |
| 2013/0016347 A1 | 1/2013 | Gono |
| 2014/0038192 A1* | 2/2014 | Buse ..................... C12Q 1/686 |
| | | 435/6.12 |
| 2015/0018645 A1 | 1/2015 | Farkas et al. |
| 2015/0377769 A1 | 12/2015 | Zeng et al. |
| 2016/0131586 A1* | 5/2016 | Gardner ............... G01N 21/658 |
| | | 356/301 |
| 2016/0363534 A1 | 12/2016 | Hagen et al. |

OTHER PUBLICATIONS

PCT International Search Report and Written Opinion, International Application No. PCT/US2016/036439, dated Nov. 15, 2016.
PCT International Preliminary Report on Patentability, International Application No. PCT/US2016/036439, dated Dec. 21, 2017.

* cited by examiner

| Interface Position | Reformatter Position |
|---|---|
| T1 | F21 |
| T2 | F20 |
| T3 | F19 |
| T4 | F18 |
| T5 | F17 |
| T6 | F26 |
| T7 | F25 |
| T8 | F16 |
| T9 | F14 |
| T10 | F13 |
| T11 | F27 |
| T12 | F24 |
| T13 | F23 |
| T14 | F12 |
| T15 | F11 |
| T16 | F28 |
| T17 | F32 |
| T18 | F6 |
| T19 | F9 |
| T20 | F10 |
| T21 | F30 |
| T22 | F31 |
| T23 | F4 |
| T24 | F5 |
| T25 | F7 |
| T26 | F33 |
| T27 | F34 |
| T28 | F35 |
| T29 | F2 |
| T30 | F3 |

FIG. 4

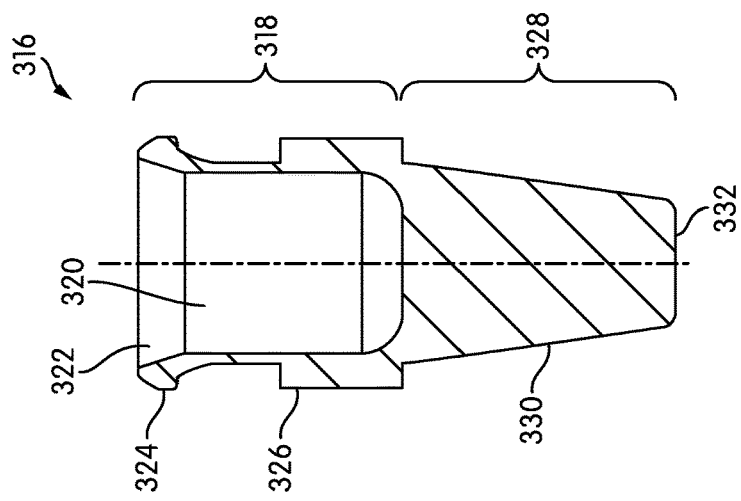
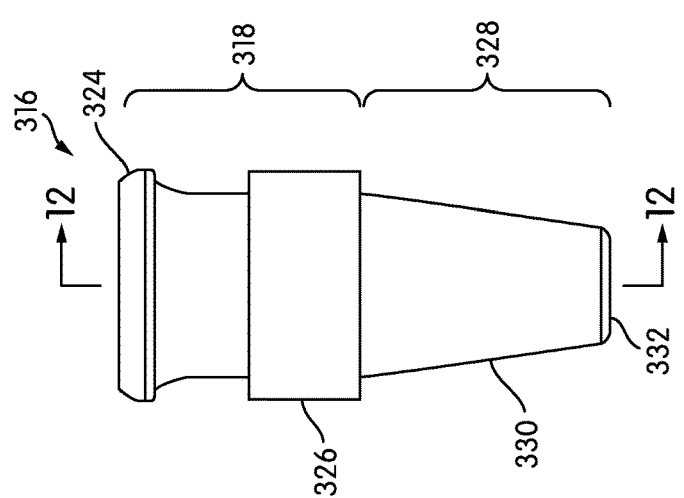
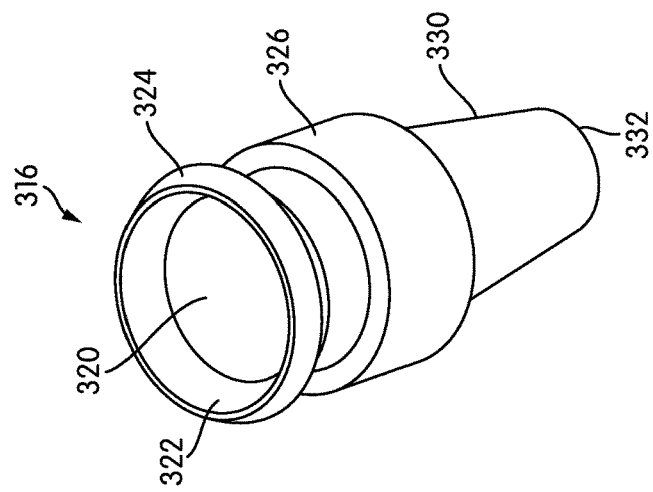

METHODS AND DEVICES EMPLOYING THERMOPLASTICS FROM THE POLYARYLETHERKETONE (PAEK) FAMILY OF SEMI-CRYSTALLINE THERMOPLASTICS FOR CALIBRATION AND/OR MONITORING OF OPTICAL MEASUREMENT DEVICES

CROSS REFERENCE TO RELATED APPLICATIONS

This application claims the benefit of U.S. Provisional Application No. 62/173,045, filed Jun. 9, 2015, which is incorporated by reference herein.

FIELD OF THE DISCLOSURE

This disclosure relates to calibrating and monitoring optical measurement devices, such as fluorometers configured to excite and then detect and measure fluorescent emission signals, by measuring the optical emission from a reference device made from a material having known optical emission properties, and, in particular, by measuring the optical emission from a reference device made from thermoplastics from the polyaryletherketone (PAEK) family of semi-crystalline thermoplastics.

BACKGROUND

None of the references described or referred to herein are admitted to be prior art.

Various industrial and commercial processes require the accurate measurement of optical electromagnetic emissions of differing wavelengths.

For example, in the field of nucleic acid diagnostics, to detect different nucleic acids of interest, different probes configured to hybridize to different nucleic acids, each of which may provide detectibly different fluorescent emission signals, can be used. Different probes configured to hybridize to different targets can be formulated with fluorophores that fluoresce at a predetermined wavelength when exposed to excitation light of a prescribed excitation wavelength. Assays for detecting different target nucleic acids can be performed by alternately exposing sample material to different excitation wavelengths and detecting the level of fluorescence at the wavelength of interest corresponding to the probe for each target nucleic acid of interest. Parallel processing can be performed using different signal-detecting devices constructed and arranged to periodically measure signal emissions during the assay process, and with different signal-detecting devices being configured to generate excitation signals of different wavelengths and to measure emission signals of different wavelengths to thereby detect the different nucleic acid of interest. Because the probe hybridizes to the targeted sequence or its complement in a manner permitting detection of a signal indicating the presence of the targeted sequence in a sample, the strength of the fluorescent signal is proportional to the amount of target sequence or its complement that is present in the sample.

In general, an optical measurement device ("OMD") configured to measure an optical emission signal (e.g., detect the presence or absence of and/or determine the intensity of) will include components for generating an excitation signal, directing the excitation signal at a target, receiving an optical emission signal from the target, and generating an electrical signal, such as a current and/or voltage, corresponding to the strength or intensity of the emission signal received. Such an OMD may comprise, for example, a fluorometer configured to direct an excitation signal of a prescribed wavelength at a target and generate an output signal, such as a current or voltage, based on receipt of a fluorescent emission signal of a prescribed wavelength from the target. Such an OMD may comprise a light-emitting element, such as a light-emitting diode (LED), a light-detecting element, such as a photodiode, optic elements, such as one or more lens(es), filter(s), mirrors, optical collimators, optical wave guides (such as optic fibers), beam splitters, etc., and integrated circuits. The OMD may include a housing or other structure on which components of the OMD are supported. Such a housing may provide a window through which excitation light passes out of the housing and emission light passes into the housing, but the housing may otherwise provide a light-tight environment to minimize the influence of stray light on the emission signal detection. The optic elements may define optic paths from the light-emitting element to the window and from the window to the light-detecting element.

Suitable signal-detecting devices include fluorometers, such as a fluorometer described below. An automated nucleic acid diagnostic instrument may be configured to process numerous samples carried in multiple receptacles, and each fluorometer may be configured to take fluorometric readings from the receptacles as they are indexed past the fluorometer, or as the fluorometer is indexed past the receptacles, for example, once every 3 seconds. Thus, 1200 times for each hour of operation of the instrument, each fluorometer generates an excitation signal that is directed at the sample receptacle and measures the emission signal emitted by the contents of the receptacle, generating an electrical signal that is proportional to the intensity of the emission signal.

OMDs, such as fluorometers, are susceptible to generating false, poor, and/or inconsistent readings for a number of reasons, including inherent differences between individual fluorometers due to the manufacturing process, malfunctioning of the OMD, and accumulation of debris in the system (primarily on or around the optic element). An OMD assembly may include numerous components and tolerances in the construction and installation of such components may exist from one OMD to the next. For example, system to system variability may be created by the stacked tolerances relating the construction and installation of light sources, optic fibers, lenses, filters, mirrors, etc. Such structural variability can lead to signal variability. Thus, the signals of the OMDs can be calibrated, i.e., standardized or normalized, to the signals of a "standard" OMD detecting an emission signal from a known emission source.

A malfunction (device failure and/or deteriorated performance) by an OMD during operation of the instrument or miscalibration of the OMD will cause errors in the optical readings generated by that OMD and thereby cause errors in the diagnostic results. Such malfunctions may be due to mechanical and/or electrical failures that occur during operation of the OMD. While operation of the OMDs can be checked during routine maintenance of the instrument, such opportunities for testing are rare, since the testing can only be performed when the instrument is shut down. In some instances, the instrument is operated continuously for extended periods of time for maximum throughput. Therefore, it becomes impractical and non-cost-effective to repeatedly shut the instrument down to perform OMD functionality testing.

Calibrating an OMD, such as a fluorometer, and/or monitoring the performance of the OMD involves typically generating an emission signal (a fluorescent reference emission) of known intensity and/or wavelength. The reference emission is detected by the OMD to be calibrated or monitored and the signal generated by the OMD from the reference signal is compared to the signal to be expected from the reference emission. For calibration, if the actual and expected signals do not agree, the OMD may be adjusted as necessary, e.g., by adjusting electronic gains in the signal processing electronics, so that the signal generated by the OMD matches the expected signal.

In the past, different mechanisms have been employed for generating reference emission signals for calibrating and/or monitoring fluorometers and other OMDs.

For example, a reference emission could be generated by a light source providing an optical signal of known intensity as well as, optionally, providing a referencing signal of a known wavelength. Such a light source may comprise a light emitting diode, a laser, or a white light and appropriate filters. Such devices are difficult and expensive to build and maintain. In addition, the output of a light source may not be stable, so that a reference emission generated b the source may not be stable. Furthermore, such devices may be relatively large and bulky and may not be suitable for calibrating or testing the OMD in its normal operating environment thereby requiring that the OMD be removed from an instrument or system in which it is employed so that it can be tested and re-calibrated.

Another mechanism for generating a reference emission is the use of controlled sources that generate known optical emission signals. Such sources may comprise fluorescent sources, such as liquid dyes. Such dyes can be placed into a receptacle, e.g., a multi-well plate, and placed into a diagnostic instrument for detection by the OMD and the signal generated by the OMD can be compared to an expected signal from the fluorescent source. Such fluorescent sources can, however, be unstable and often have special storage requirements and pre-use preparation procedures. For example, liquid dyes may need to be stored in a frozen state and require special preparation procedures prior to their use. In addition, such sources may be unstable and may need to be used within a relatively short period of time following their preparation. Fluorescent dyes may also be susceptible to photo-bleaching, whereby repeated exposure of the fluorescent source to an excitation light signal may alter the emission signal over a period of time.

A third mechanism for generating a reference emission is to use emissive plastics, such as fluorescent plastics. Typical plastics used to date fluoresce at certain specific wavelengths (i.e. colors), and thus different plastics or differently-colored plastics are required for testing different fluorometers configured to detect emissions of different wavelengths. In addition, fluorescent plastics used today can be unstable and degrade over time and are susceptible to photo-bleaching. Thus, the reference emission signals generated by such plastics can be degraded over time and/or after repeated exposures to an excitation signal.

Accordingly, a need exists for means and methodologies for periodically confirming the proper functionality of the OMDs during the operation of the instrument as well as for calibrating or standardizing multiple OMDs so that they generate consistent readings.

SUMMARY

The following presents a simplified summary in order to provide a basic understanding of some aspects described herein. This summary is not an extensive overview of the claimed subject matter. It is intended to neither identify key or critical elements of the subject matter disclosed herein nor delineate the scope thereof. Its sole purpose is to present some concepts in a simplified form as a prelude to the more detailed description that is presented later.

Aspects of the disclosure are embodied in an optical signal detection module comprising an optical measurement device configured to detect an optical emission signal from an optical emission source placed in a signal-detecting position with respect to the optical measurement device and a cover element positioned with respect to the signal-detecting position of the optical measurement device and moveable between a closed position covering the signal-detecting position and an open position not covering the signal-detecting position. The cover element includes an inner surface comprising a material that emits a stable and repeatable reference emission that can be detected by the optical measurement. The cover element is configured so that when the cover element is in the closed position, the inner surface is in the signal-detecting position with respect to the optical measurement device so that the optical measurement device is exposed to the reference emission.

According to further aspects, the inner surface of the cover element comprises a thermoplastic from the polyaryletherketone (PAEK) family of semi-crystalline thermoplastics.

According to further aspects, the inner surface of the cover element comprises polyether ether ketone (PEEK).

According to further aspects, the optical measurement device comprises a fluorometer.

Aspects of the disclosure are also embodied in a reference device for calibrating or monitoring the performance of an optical measurement device. The reference device is formed at least partially from a thermoplastic from the polyaryletherketone (PAEK) family of semi-crystalline thermoplastics and is configured to be placed in a signal-detecting position with respect to the optical measurement device, whereby the portion of the reference device formed from PAEK will emit a stable and repeatable reference emission that can be detected by the optical measurement device.

According to further aspects, the thermoplastic comprises polyether ether ketone (PEEK).

Aspects of the disclosure are also embodied in a method for calibrating or monitoring the performance of an optical measurement device using a transfer mechanism that comprises a robotic pipettor or pick and place mechanism. A portion of the transfer mechanism is formed from an optical reference material or the transfer mechanism has removably attached thereto a reference device formed at least partially from an optical reference material. The optical reference material emits a stable and repeatable reference emission that can be detected by the optical measurement device. The method comprises moving a portion of the transfer mechanism into a signal-detecting position with respect to the optical measurement device so that the optical measurement device can detect a reference emission from the transfer mechanism or from the reference device removably attached to the transfer mechanism. An output representative of the emission detected by the optical measurement device is generated by the optical measurement device. The output is compared to an expected output for the reference emission to calibrate or monitor the performance of the optical measurement device.

According to further aspects, the optical reference material comprises a thermoplastic from the polyaryletherketone (PAEK) family of semi-crystalline thermoplastics.

According to further aspects, the optical reference material comprises polyether ether ketone (PEEK).

A method for calibrating or monitoring the performance of an optical measurement device in a sample processing instrument configured to measure an optical emission from the contents of a sample receptacle. The sample processing instrument includes receptacle holding structure configured to hold a sample vial in a signal-detecting position with respect to the optical measurement device. The method comprises providing a reference device formed at least partially from an optical reference material that emits a stable and repeatable reference emission. The reference device is formed in the shape of a sample receptacle and is configured to be held by the receptacle holding structure in the signal-detecting position with respect to the optical measurement device. An emission from the reference device located in the signal-detecting position with respect to the optical measurement device is detected using the optical measurement device. An output representative of the emission detected by the optical measurement device is generated with the optical measurement device. The output s compared to an expected output for the reference emission to calibrate or monitor the performance of the optical measurement device.

According to further aspects, the optical reference material comprises a thermoplastic from the polyaryletherketone (PAEK) family of semi-crystalline thermoplastics.

According to further aspects, the optical reference material comprises polyether ether ketone (PEEK).

According to further aspects, the reference device includes a channel formed therein with a reference plug formed from the optical reference material disposed within the channel, and wherein detecting an emission from the reference device comprises using the optical measurement device to detect an emission from the reference plug located in the signal-detecting position with respect to the optical measurement device.

Other features and characteristics of the present disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various, non-limiting embodiments of the present disclosure. In the drawings, common reference numbers indicate identical or functionally similar elements.

FIG. 4 is a table showing mapping between the interface fiber positions and the baseplate fiber positions shown in FIGS. 2 and 3.

FIG. 10 is a perspective view of an optical reference standard vial.

FIG. 11 is a side view of the optical reference vial.

FIG. 12 is a cross-sectional view of the optical reference vial along the line 12-12 in FIG. 11.

DETAILED DESCRIPTION

Figure 1:
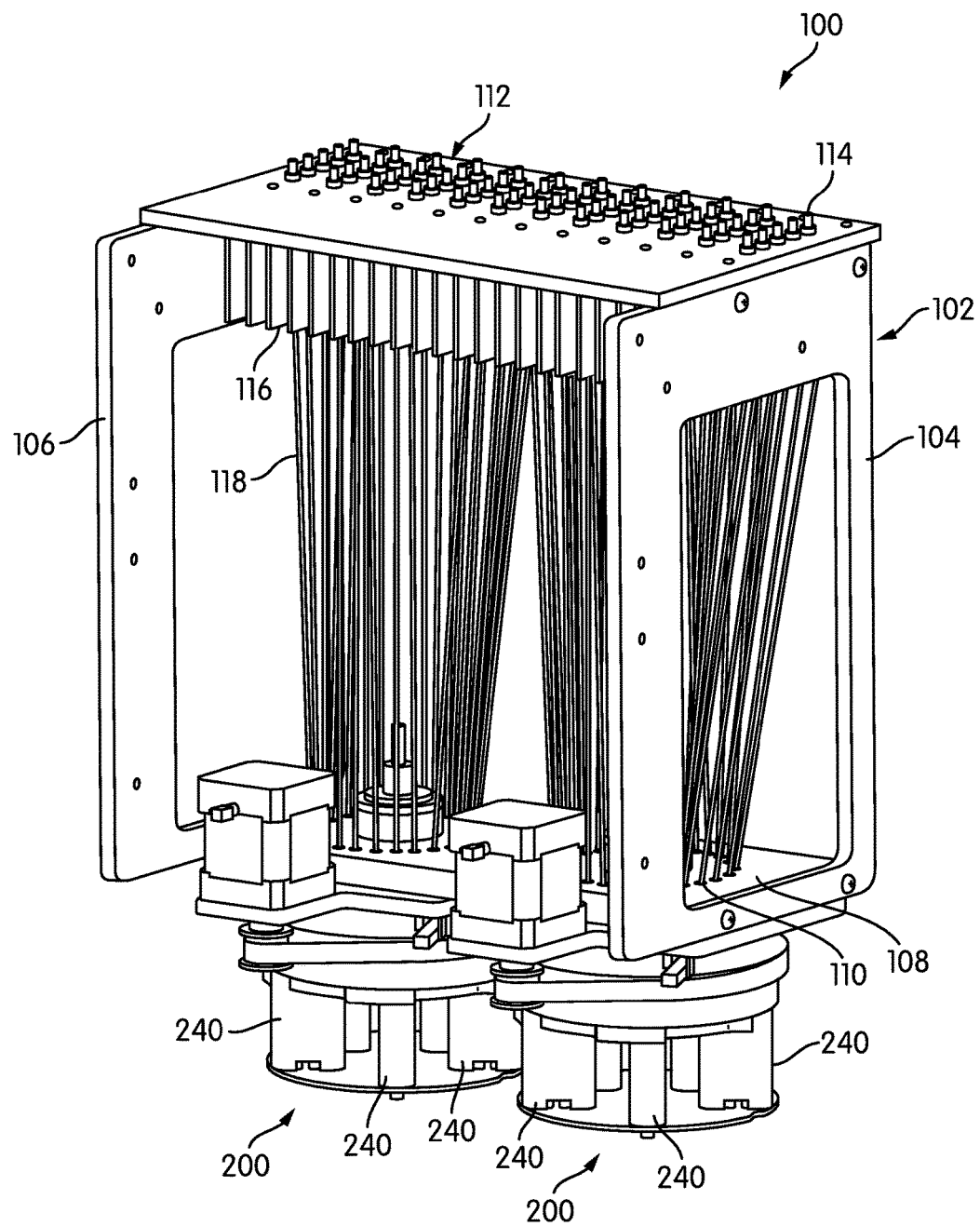
FIG. 1 is a perspective view of a signal detection module including a fiber reformatter frame.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Aspects of the disclosure are embodied in methods, systems, and devices for calibrating (or standardizing) optical measurement devices ("OMDs"), such as fluorometers configured to detect and measure fluorescent signals, and/or for monitoring the performance of OMDs. The calibration or monitoring is performed by using the OMD to measure or detect an optical emission (referred to herein as a "reference emission") from a device or structure made from a material having known optical emission properties (referred to herein as a "reference device") and comparing the output of the OMD to an expected output for a properly calibrated and properly functioning OMD exposed to the reference emission. The material from which the reference device is made can be a thermoplastic from the polyaryletherketone ("PAEK") family of semi-crystalline thermoplastics, such as polyether ether ketone ("PEEK").

PEEK and similar semi-crystalline thermoplastics have been found to be reliable and effective materials for construction of reference devices. Structurally, PEEK is strong, durable, heat-resistant, and machinable and thus is ideally suited for constructing reference devices of nearly any physical configuration and can withstand most any environment in which an OMD is likely to be employed. Optically, it has been found that PEEK provides a strong fluorescent reference emission when exposed to excitation light and will fluoresce across the entire spectrum of anticipated wavelengths. The fluorescent properties of PEEK have been found to be remarkably stable over time. For example, PEEK has been found to be high resistant to photo-bleaching compared to other materials. Thus, a reference device made from PEEK can be expected to be usable for a significantly long time (e.g., 10 or more years). Thus, PEEK and similar materials emit a stable and repeatable reference emission and can be used to calibrate and monitor OMDs configured to detect optical emissions at many different wavelengths. In various embodiments, the emission is repeatable in the sense that every emission from a particular reference device can be expected to be similar within a relatively small range of variation. In various embodiments, the emission is also repeatable in the sense that different portions of a reference device made from a common lot of reference material can be expected to have comparable emissions. In various embodiments, the emission is stable in the sense that the emission does not change appreciably over time under normal use conditions.

When a new reference device is made from PEEK, it can first be "characterized" before it can be used for calibrating or monitoring OMDs. While the optical properties of a particular piece of PEEK material have been found to be consistent and repeatable across the optical spectrum, it has been found that the optical properties of different pieces of PEEK—e.g., from different lots of material or different manufacturers may vary by as much as 50%. The new reference device is characterized by placing it in the position in which it is expected to be used for calibrating and monitoring, and emission reference signals from the reference device are measured with a "standard" OMD known to be properly calibrated and operating properly. An expected reference signal for that reference device is recorded, and that recorded reference signal will be compared with emission signals detected by other OMDs for calibrating the OMDs (i.e. standardizing them to the "standard" OMD) and/or for monitoring the performance of the OMDs. The recorded reference signal may be derived from multiple reference readings from one or more standard OMDs. For example, the recorded reference signal may be a numerical average of multiple signals. In addition, different expected reference signals may be recorded for different fluorescent wavelengths that are expected to be measured with the OMD. For example, fluorometer signals are often expressed in RFUs (relative fluorescent units) to define a relative magnitude of an emission signal. The reference device may be characterized to emit a first RFU level at a first excitation wavelength, a second RFU level at a second excitation wavelength, a third RFU level at a third excitation wavelength, etc.

Throughout this disclosure, reference devices will be described as manufactured entirely or partially from PEEK, although it should be understood that other materials in the PAEK family may be suitable as well.

In exemplary embodiments described herein, the reference device is incorporated into a portion of the structure of the OMD or into a portion of the structure of a diagnostic instrument in which the OMD is incorporated. For example, in an embodiment described below, the reference device is incorporated into a lid configured to cover emission-receiving ends of optic fibers that can be coupled to a fluorometer configured to detect emission signal transported by the fiber to the fluorometer. Alternatively, or in addition, the reference device is configured as a component or in the shape of a component that is used in conjunction with the OMD. For example, in another embodiment described below, the reference device is formed from PEEK completely or partially in the shape of a receptacle vial that can be operatively positioned in a signal-detecting position with respect to optic fibers in a receptacle holding structure. In either embodiment, the OMD can be monitored and/or calibrated while operating the OMD in an essentially normal operating mode and without having to disassemble the OMD or a device in which the OMD is incorporated.

In another aspect of the disclosure, a master reference device is made from PEEK, that master reference device is characterized by a standard OMD to determine a reading that would be expected from other similar OMDs reading the master reference device, and the output of each OMD is adjusted so that its output matches that of the standard OMD, thereby calibrating or standardizing all OMDs to the standard OMD. In various embodiments, the standard OMD is only used for characterizing reference device; i.e., it may not be used in a production diagnostic instrument assay results. Thus, the standard OMD sees relatively little use and can be expected to experience limited wear that might otherwise affect the performance of the OMD.

In accordance with an aspect of this disclosure relating to reference devices that are incorporated into a portion of the structure of a diagnostic instrument in which the OMD is incorporated or to reference devices that are configured as a component—or in the shape of a component—that is used in conjunction with the OMD, an exemplary device in which an OMD is incorporated and for which a reference device made from PEEK may be used to calibrate and/or monitor the output of the OMD is described below.

Detection and, optionally, measurement of emission signals from emission signal sources, such as receptacles containing reaction materials undergoing a diagnostic procedure e.g., a nucleic acid diagnostic assay) can be performed with a signal detection module, such as exemplary optical signal detection module 100 shown in FIG. 1. While described below, further details of the module and related aspects can be found in United States Patent Application Publication No. 2014-0263984 entitled "Indexing Signal Detection Module." The signal detection module 100 may be incorporated into a processing module (not shown), such as an incubator, which includes a plurality of receptacle holders, each configured to hold one or more receptacles and constructed and arranged to impart thermal energy to the receptacles held thereby to change and/or maintain the temperature of the contents of each receptacle. An exemplary processing module includes an incubator as disclosed in U.S. Patent Application Publication No. 2014-0038192, entitled "System, Method, and Apparatus for Automated Incubation."

The signal detection module includes a reformatter frame 102. In general, the reformatter frame includes sides 104, 106, abuse 108 within which are formed a plurality of fiber-positioning holes 110, and an interface plate 112 attached to an upper end of the reformatter frame 102. Note that the designation of the reformatter frame 102 as being upright or the sides 104, 106 as being vertical is merely to provide a convenient reference with respect to the orientation of the signal detection module 100 as shown in FIG. 1, and such terms of orientation are not intended to be limiting. Accordingly, the signal detection module 100 could be oriented at any angle, including vertical, horizontal, upside down, or any angle therebetween.

Optical waveguides, such as optical transmission fibers 118, extend between the interface plate 112 and the base 108 of the reformatter frame 102. In the present context, an optical transmission fiber, or optical fiber, comprises a flexible, transparent rod made of glass (silica) or plastic that functions as a waveguide, or light pipe, to transmit light between the two ends of the fiber. Optical fibers typically include a transparent core surrounded by an opaque or transparent cladding material having a lower index of refraction than the core material. A light transmission is maintained within the core by total internal reflection. Each optical fiber may comprise a single fiber having a single fiber core, or each fiber may comprise a fiber bundle of two or more fibers.

The reformatter frame 102 is constructed and arranged to reconfigure the relative spatial arrangements of the fibers 118 from their first ends to their second ends so as to rearrange the transmission fibers 118 into a spatial arrangement in which they can be more efficiently interrogated by an OMD to measure a signal transmitted therethrough. In the context of this description, the first end of the fiber 118 corresponds to the end of the fiber closest to the signal emission source being measured, and the second end of the fiber corresponds to the end of the fiber closest to the OMD. This is merely a convenient convention for distinguishing one end of the transmission fiber 118 from another end of the transmission fiber 118. Otherwise, the designation of the ends of the fibers as being a first end or a second end is arbitrary.

The first ends of the transmission fibers 118 are attached to the interface plate 112, for example extending into or through openings formed through the interface plate 112. Signal coupling elements 114, e.g., ferrules, may be provided in each of the openings formed in the interface plate 112 for securely attaching each optical transmission fiber 118 to the interface plate 112. Although not shown in FIG. 1, each opening formed in the interface plate 112 may be in signal transmission communication with an emission signal source. In one embodiment, a signal emission source may comprise a receptacle containing the contents of a chemical or biological assay. In the case of optical emission signals, the receptacles may be positioned and held so as to optically isolate each receptacle from the surrounding receptacles. In addition, the receptacles may be held within an incubator device located in optical communication with the interface plate 112 and configured to alter the temperature of receptacles or maintain the receptacles at a specified temperature, in such an application, the interface plate 112 can be formed of a suitably heat-conducting material, such as aluminum or copper, and that the interface plate 112 further include heat dissipating fins 116 formed on one side of the interface plate 112 for dissipating heat from the interface plate 112. A fan (not shown) may be provided to enhance heat dissipation via the fins 116. Also, coupling elements (ferrules) 114 may be thermally insulating to insulate the transmission fibers 118 from the heat of the receptacles held within the incubator. Suitable insulating materials include Delrin®, black PVC, or black Valox®.

In the embodiment illustrated in FIG. 1, the transmission fibers 118 are attached to the interface plate 112 in a rectangular configuration comprising a plurality of rows, each row having one or more transmission fibers 118. As shown in the illustrated embodiment, in an application in which the interface plate 112 includes heat dissipating fins 116, the transmission fibers 118 may extend between adjacent fins 116 into an associated opening formed in the interface plate 112. The illustrated embodiment includes twelve rows of five transmission fibers 118 each, for a total of sixty transmission fibers that can be employed for interrogating up to sixty individual emission sources, such as reaction receptacles containing reaction materials therein.

The second ends of the transmission fibers 118 are connected to the base 108 of the reformatter frame 102, for example, by being aligned with or inserted into or through fiber-positioning holes 110. The fiber-positioning holes 110 may be in a spatial arrangement that is different from the spatial arrangement of the fiber-receiving holes formed in the interface plate 112 and are in a position that can be more efficiently interrogated by one or more OMDs. In the illustrated embodiment, the fiber position holes 110 are arranged in two circles. Other spatial arrangements are contemplated, including, two or more concentric circles, one or more open rectangles, one or more ovals, etc.

In the illustrated embodiment, two signal detector heads 200 are attached to a lower end of the reformatter frame 102. Each of the signal detector heads hold one or more OMDs 240 and are configured to move the OMDs with respect to the reformatter frame and to sequentially place each OMD into an operative, signal-detecting position with respect to each of the second ends of the transmission fibers 118. Further details of the signal detector head are described below.

Figure 2:
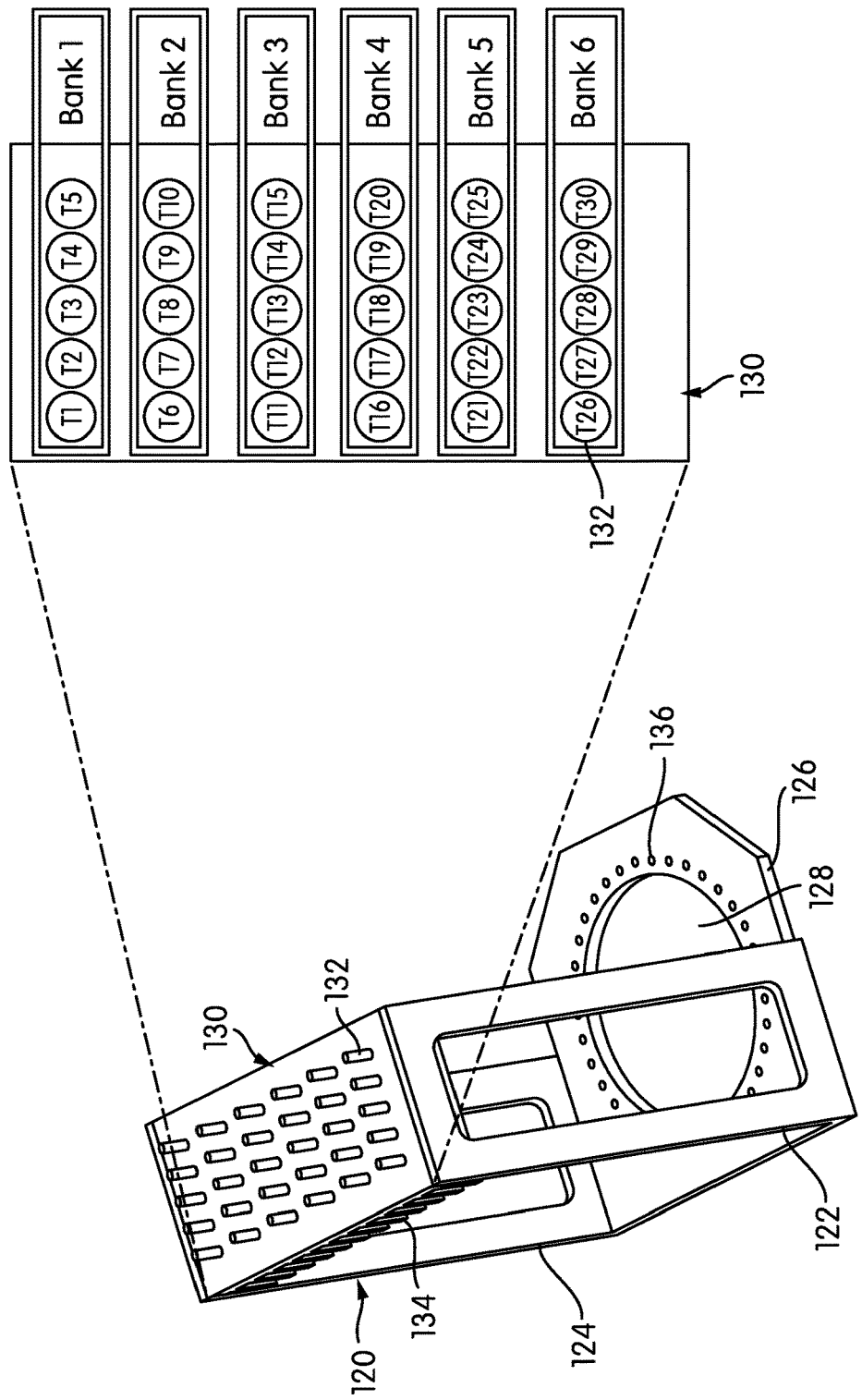
FIG. 2 is a perspective view of an exemplary fiber reformatter frame showing a fiber position mapping in an interface plate of the frame.
Figure 3:
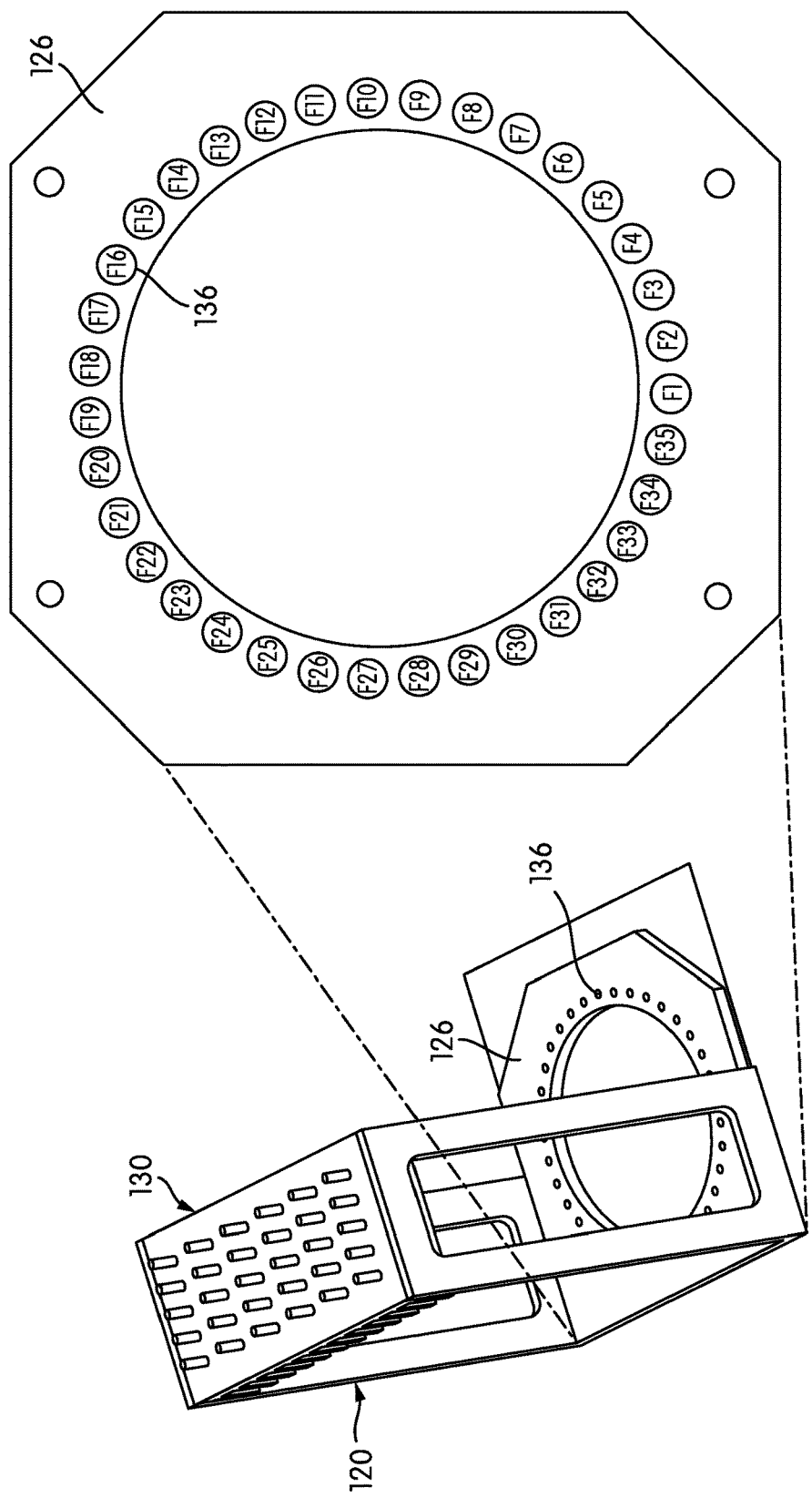
FIG. 3 is a perspective view of the fiber reformatter frame showing a fiber position mapping in a baseplate of the frame.

FIGS. 2 and 3 are perspective views of an alternative embodiment of a reformatter frame 120—shown without transmission fibers installed thereon. Reformatter frame 120 includes sides 122, 124 and abase 126 having an opening 128 formed therein with a plurality of fiber-positioning holes 136 positioned around the opening 128 in a generally circular configuration. An interface plate 130 is attached to the sides 122, 124 of the frame 120 at an end thereof opposite the base 126. Interface plate 130 includes a plurality of signal coupling elements 132, e.g., ferrules, and may include heat dissipating fins 134 disposed on a side of the interface plate 130 opposite the coupling elements 132. Each coupling element 132 corresponds to a fiber-receiving opening formed through the interface plate 130. As can be seen in FIGS. 2 and 3, the coupling elements 132 are arranged in a rectangular configuration of six rows of five coupling elements each. The number of openings 136 formed in the base 126 can correspond to the number of coupling elements 132 formed in the interface plate 130. FIG. 2 also shows an exemplary mapping of the spatial arrangement of fiber positions in the interface plate 130 of the reformatter frame 120. As shown in FIG. 2, the interface plate 130 includes six rows, or banks, of five fiber positions each, designated T1-T5, T6-T10, T11-T15, T16-T20, T21-T25, and T26-T30, for a total of thirty fiber positions.

FIG. 3 shows a mapping of the spatial arrangement of fiber positions of the fiber-positioning holes 136 formed in the base 126 of the reformatter frame 120. In the illustrated embodiment, 35 fiber-positioning holes 136 are formed in the base 126, and are designated F1, F2, F3, F4, . . . F35, starting at the lower six o'clock) position with respect to the opening 128.

FIG. 4 is a table showing an exemplary mapping of the rectangularly-arranged interface positions T1-T30 in the interface plate 130 to thirty of the circularly-arranged fiber-positioning hole positions F1-F35 in the base 126. Note that the fiber positions are not mapped T1-F1, T2-F2, T3-F3, T4-F4, etc.

The mapping shown in FIG. 4 is exemplary only; other mappings between the fiber positions in the interface plate 130 and the fiber positions in the base 126 may be used. A goal in running the fibers from the base 108 to the interface plate 112 is to limit bending in each of the fibers, and any mapping that addresses this goal may be suitable. In this embodiment, the number of interface positions in the interface plate 130 is exceeded by the number of fiber-positioning holes in the base 126 (e.g., 30 vs. 35). Fluorescent calibration targets can be placed in the additional fiber-positioning holes in the base to test and/or calibrate the signal detectors of the signal detector head 200.

In an alternative embodiment, the number of interface positions in the interface plate 130 is equal to the number of fiber-positioning holes in the base 126 (e.g., 30).

Figure 5:
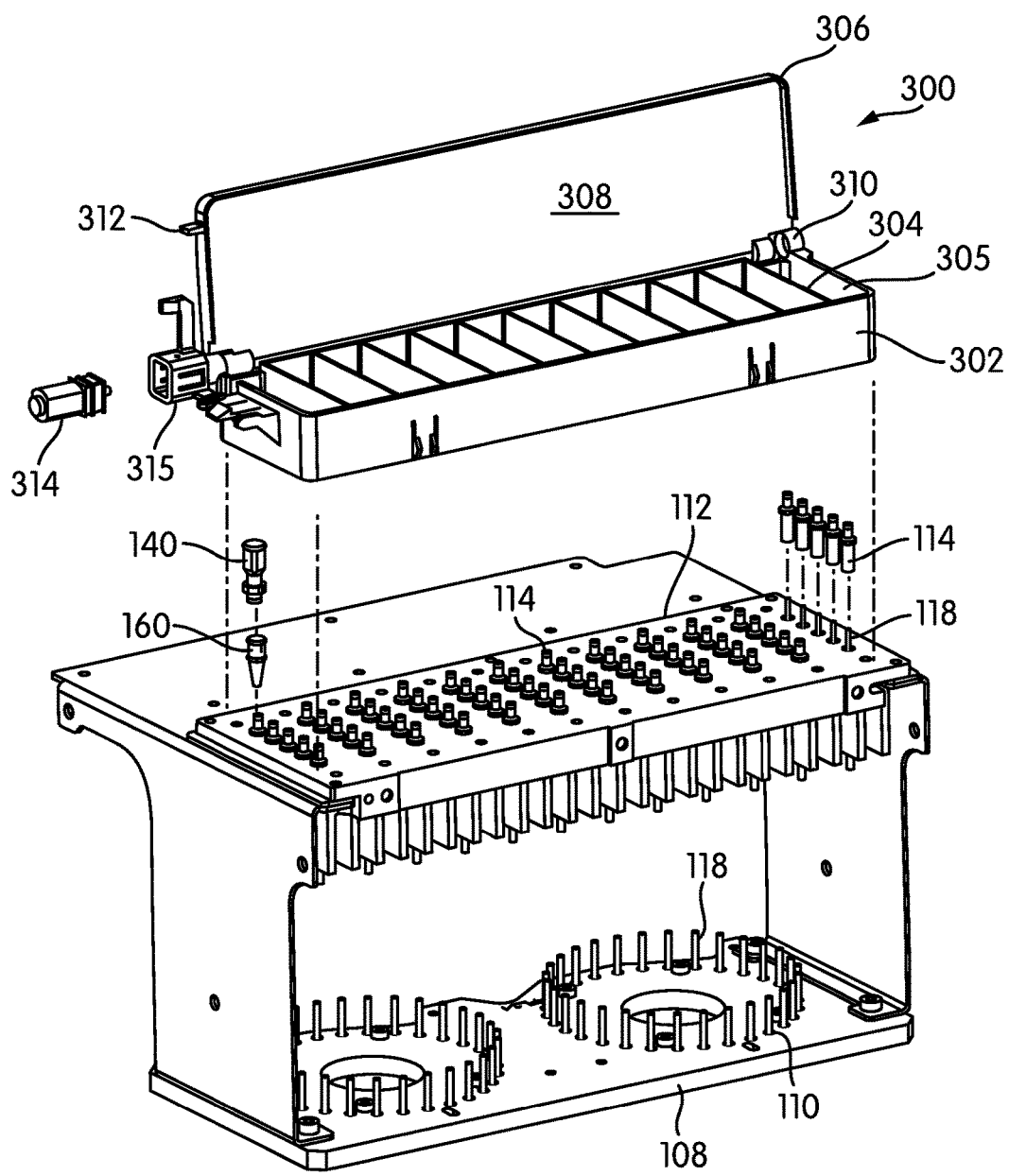
FIG. 5 is an exploded perspective view of a fiber reformatter frame and a lid assembly, with the lid in an open position.

As shown in FIG. 5, an exploded view of a fiber reformatter frame, the signal detection module may include a lid assembly 300 supported on the interface plate 112 of the reformatter frame. As explained above, the reformatter frame may include a plurality of optical fibers 118 extending through fiber positioning holes 110 in the base 108 of the frame up and through corresponding holes formed in the interface plate 112 where they may be connected to signal coupling elements, such as ferrules 114. For simplification, FIG. 5 shows only upper and lower portions of the optical fibers 118.

Figure 6:
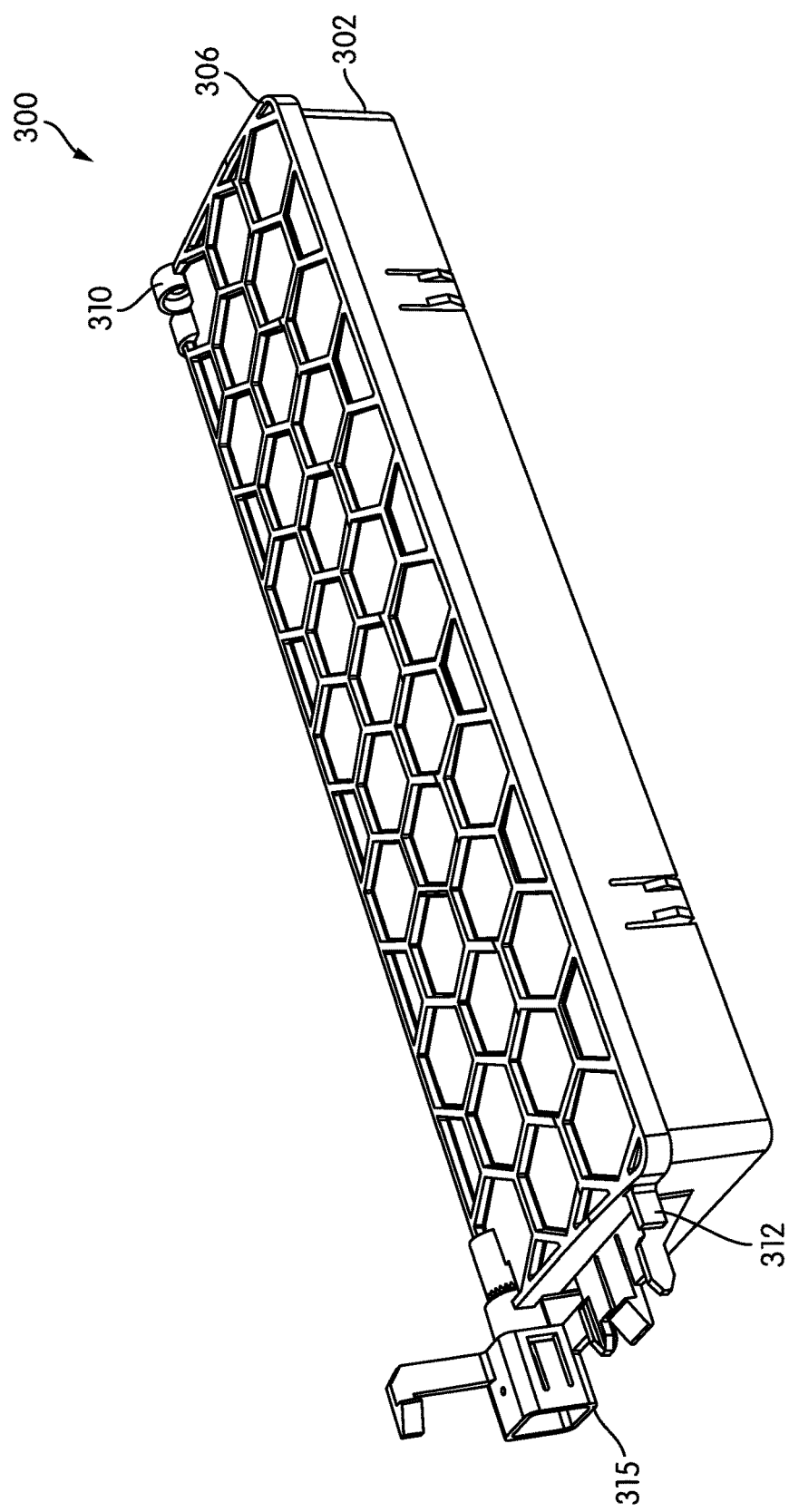
FIG. 6 is a perspective view of the lid assembly, with the lid in a closed position.

As shown in FIGS. 5 and 6, the lid assembly 300 includes a frame 302 that is supported on the interface plate 112. Frame 302 includes a plurality of separator walls 304 extending between opposed sides of the frame 302, thereby defining discrete compartments 305 between adjacent walls. Each compartment 305 contains one row of signal coupling elements 114.

The lid assembly 300 further includes a cover element, such as lid 306, mounted with respect to the frame 302 so as to be moveable between an open position as shown in FIG. 5, and a closed position resting on top of the frame 302, as shown in FIG. 6, thereby covering each of the compartments 305 and the rows of signal coupling elements 114 contained therein. In the illustrated embodiment, the lid 306 is a pivoting lid that is moveable about a hinge axis 310 between the open position and a closed position.

In various embodiments, the lid assembly 300 includes a mechanism configured to effect powered movement of the lid 306 between the open and closed positions. For example, a micromotor 314 may be provided within a motor casing 315 for effecting powered, hingewise movement of the lid 306 between the open and closed positions. In various embodiments, a sensor may be provided for automated detection of a position of the lid 306 with respect to the frame 302. For example, an indicator tab 312 extending from a portion of the lid 306 may cooperate with one or more detection devices, such as slotted optical sensors (not shown), for detecting a position of the lid 306.

As will be explained in further detail below, the optical fibers 118 are configured to transmit an optical signal between an MID positioned at a first end of the optical fiber 118, below the base 108, and a second end at the signal coupling device 114 so as to detect an optical signal from an optical signal source positioned above the signal coupling element 114. In one embodiment, the optical signal source may comprise a receptacle vial 160 positioned above each of one or more of the fibers 118 (above the corresponding signal coupling element 114). Receptacle vial 160 may contain a chemical or biological substance that fluoresces under certain conditions and when exposed to an optical excitation signal. The vial 160 may be closed by a cap 140 that is configured to provide a snap connection between the cap 140 and the vial 160 and is further configured to be manipulated (e.g., picked up and moved) by a receptacle transport mechanism, such as a robotic pick and place mechanism, as will be described in further detail below. Receptacle holding structures not shown) may be provided above the rows of signal coupling elements 114. Such holding structures may be configured to hold each receptacle 160 in a signal-detecting position with respect to a corresponding fiber 118 and signal coupling element 114 and to optically isolate each receptacle 160 from adjacent receptacles. Further details of exemplary receptacle holding structures are provided in U.S. Patent Application Publication No. 2014-0038192.

The size of the receptacle vial 160 and the cap 140 when in their connected configuration is such that the assembled vial and cap will fit within the compartment 305 of the lid assembly 300 so that the lid 306 can be closed over the assembled receptacle vial 160 and cap 140 operatively positioned above a respective signal coupling element 114.

Figure 7:
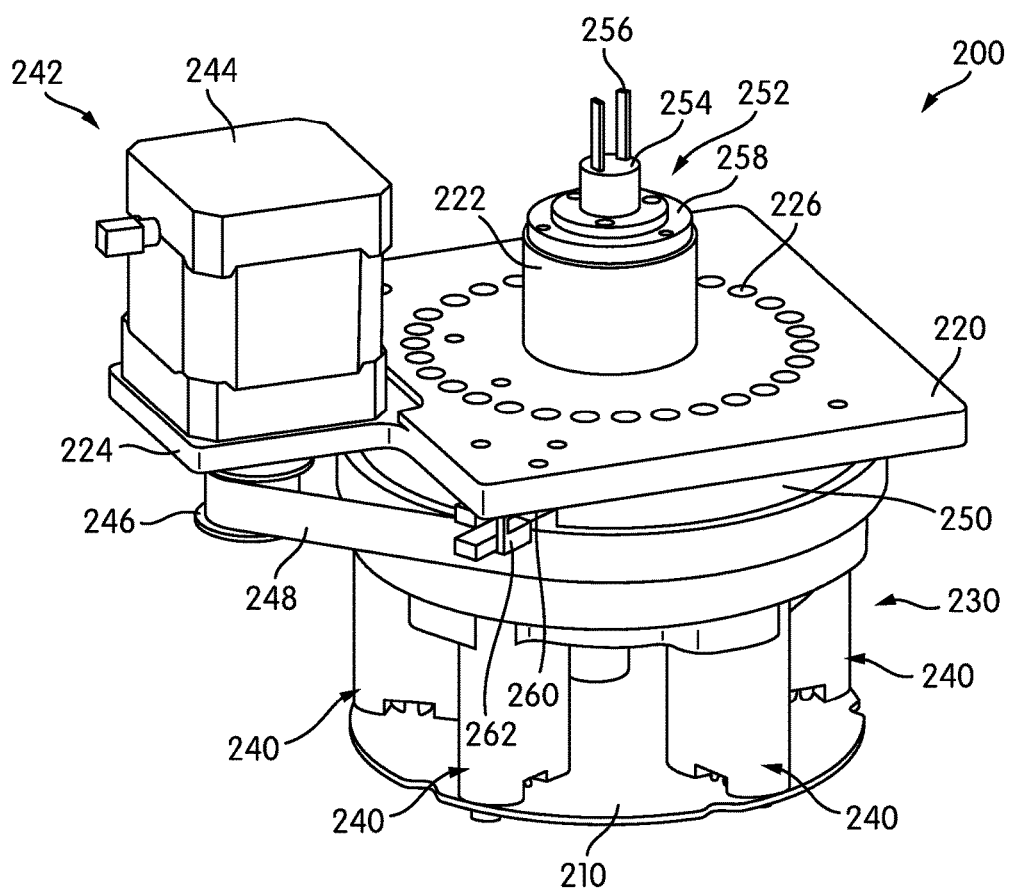
FIG. 7 is a perspective view of a signal detector head of a signal detection module.

An exemplary signal detector head 200 is shown in FIG. 7. The signal detector head 200 may be attached to a reformatter frame 102/120 and is constructed and arranged to index one or more OMDs 240 into operative positions with respect to each transmission fiber disposed in a fiber-positioning hole of the base of the reformatter frame, in the present context, an OMD is in an "operative position" with respect to a transmission fiber, or other source of optical emission, if the OMD is spatially positioned (located and oriented) to direct an excitation signal at an input portion of the fiber e.g., a proximal end) or directly at the optical emission source so that sufficient excitation energy will reach the optical emission source directly or via the fiber and to receive a detectable amount of an emission signal from a portion of the fiber (e.g., the proximal end) or directly from the optical emission source.

Although signal detector head 200 is configured to be coupled to any reformatter frame, including reformatter frames 102/120 described herein, for simplicity of the description, the signal detector head 200 will be described in the context of its implementation on reformatter frame 102 shown in FIG. 1.

In the embodiment shown in FIG. 7, the signal detector head 200 includes abase plate 220 configured to be attached to the base 108 of the reformatter frame 102 and including a plurality of fiber tunnels 226 arranged in a configuration corresponding to the spatial arrangement of fiber-positioning holes 110 formed in the base 108 of the reformatter frame 102 so that each fiber tunnel 226 will align with a corresponding one of the fiber-positioning holes 110.

In general, the signal detector head is configured to move one or more OMDs 240 to sequentially place each OMD 240 into an operative position with respect to each transmission fiber 118 to detect a signal transmitted by the transmission fiber. The signal detector head 200 further includes a detector carrier 230, which, in the illustrated embodiment, comprises a carousel that carries a plurality of OMDs 240 in a circular pattern. In the illustrated embodiment, the signal detector head 200 includes six individual OMDs 240, each mounted on a printed circuit board 210 and each configured to excite and detect a different emission signal or an emission signal having different characteristics, such as fluorescent emissions of different wavelengths.

The detector carrier 230 is configured so as to be rotatable with respect to the base plate 220. A detector drive system 242 constructed and arranged to effect powered movement, e.g., rotation, of the detector carrier 230 includes a drive motor 244 supported on a motor mount portion 224 of the base plate 220. A drive belt 248 is disposed on an output shaft wheel 246 of the motor 244 and around a pulley wheel 250 that is attached to or part of the detector carrier 230. As can be appreciated, rotation of the output shaft wheel 246 of the motor 244 causes a corresponding rotation of the pulley wheel 250 and the detector carrier 230 via the belt 248.

Motor 244 can be a stepper motor and may include a rotary encoder. The detector carrier 230 may include one or more positional or status feedback sensors. For example, the detector carrier 230 may include a home flag 260 that is detected by an optical detector 262 for indicating a rotational "home" position of the carrier 230. Optical sensor 262 may comprise a slotted optical sensor comprising an optical transmitter and receiver in which the path between the transmitter and receiver is broken by the passage of the home flag 260. Persons of ordinary skill in the art will recognize, however, that other sensors for indicating a home position may be used. Such sensors may comprise proximity sensors, magnetic sensors, capacitive sensors, etc.

A rotary connector transmits data and/or power signals between the rotating detector carrier 230 and the OMDs 240 carried thereon, and a non-rotating reference environment, such as an external controller and power source.

Further details of the signal detector head 200 as well as alternative signal detector head configurations are described in United States Patent Application Publication No. 2014-0263984.

Figure 19:
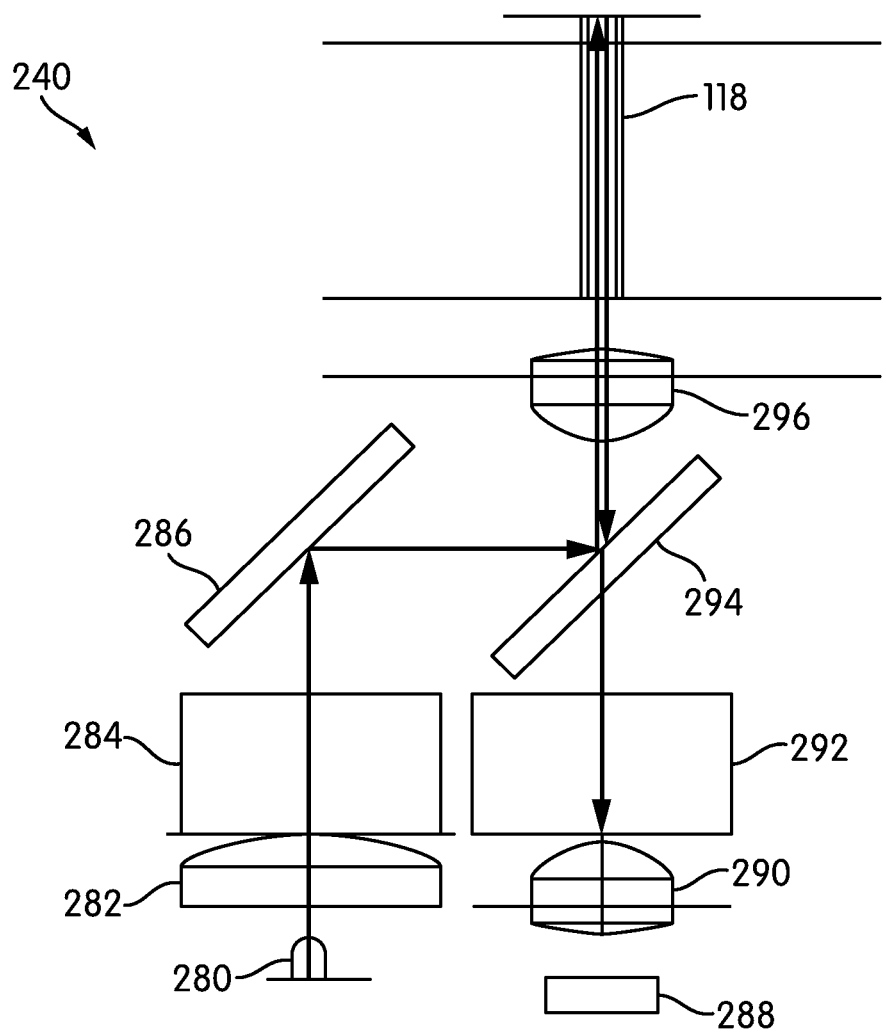
FIG. 19 is a schematic view of an embodiment of an exemplary optical path within an optical measurement device.

Operation of the OMD 240 in an exemplary embodiment is illustrated schematically in FIG. 19. The detector 240 shown is a fluorometer that is constructed and arranged to generate an excitation signal of a particular, predetermined wavelength that is directed at a potential source of fluorescent emission, such as the contents of a receptacle undergoing a diagnostic procedure to determine if a probe or marker having a corresponding emission signal of a known wavelength is present. When the signal detector head 200 includes multiple fluorometers—e.g., six—each fluorometer may be configured to excite and detect an emission signal having a different wavelength to detect a different label associated with a different probe hybridized to a different target analyte.

An excitation signal is emitted by an excitation source 280, such as an LEI), which may generate light at a predetermined wavelength, e.g. red, green, or blue light. Light from the source 280 passes through and is focused by an excitation lens 282 and then passes through an excitation filter 284. As noted, FIG. 19 is a schematic representation of the signal detector 240, and the focusing functionality provided by the excitation lens 282 may be effected by one or more separate lenses disposed before and/or after the filter element 284. Similarly, the filter functionality provided by the filter element 284 may be effected by one or more individual filters disposed before and/or after the one or more lenses that provide the focusing functionality. Filter element 284 may comprise a low band pass filter and a high band pass filter so as to transmit a narrow wavelength band of light therethrough. Light passing through the excitation lens 282 and excitation filter element 284 is reflected laterally by the mirror 286 toward a dichroic beam splitter 294. The dichroic beam splitter 294 is constructed and arranged to reflect substantially all of the light that is within the desired excitation wavelength range toward the Objective lens 296 while allowing light that is not in the wavelength range to pass through the beam splitter. From the objective lens 294, excitation light passes into a transmission fiber 118 and toward an emission source at the opposite end thereof so as to expose the source to the excitation signal.

At least a portion of any emission that is excited by the excitation signal enters the transmission fiber 118 and passes back through the Objective lens 296, from which the emission light is focused toward the dichroic beam splitter 294. Dichroic beam splitter 294 is configured to transmit light of a particular target emission wavelength range toward the emission filter 92 and the emission lens 290 and to reflect light that is not within the target emission wavelength range. Again, the filtering functionality provided by the emission filter 292 may be effected by one or more filter elements and may comprise a high band pass and low band pass filter that together transmit a specified range of emission wavelength that encompasses a target emission wavelength. The emission light is focused by the emission lens 290, which may comprise one or more lenses disposed before and/or after the filter element(s) represented by emission filter 292. The emission lens 290 thereafter focuses the emission light of the target wavelength at the detector 288, which may comprise a photodiode and which generates a voltage signal corresponding to the intensity of the emission light at the prescribed target wavelength that impinges the detector.

As the detector carrier 230 rotates, each of the OMDs 240 is sequentially placed in an operative position with respect to a second end of a different transmission fiber 118 to interrogate (i.e., measure a signal from an emission signal source located at a first end of the transmission fiber 118. The detector carrier 230 pauses momentarily at each transmission fiber 118 to permit the OMD 240 to detect an emission signal transmitted through the transmission fiber 118. Where the OMD 240 is a fluorometer, the detector carrier pauses momentarily to permit the signal detector to generate an excitation signal of a specified wavelength that is transmitted by the transmission fiber 118 to the emission signal source (receptacle) and to detect fluorescence of a specified wavelength excited by the excitation signal that is emitted by the contents of the receptacle and transmitted by the transmission fiber 118 to the fluorometer. Thus, in an embodiment, each transmission fiber 118 can be employed to transmit both an excitation signal and the corresponding emission signal, and each OMD can be used to scan multiple transmission fibers and associated emission signal sources.

The emission signal source associated with each transmission fiber 118 is interrogated once by each OMD 240 for every revolution of the detector carrier 230. Where the signal detector head 200 includes multiple OMDs 240 configured to detect different signals (e.g. emission signals of different wavelengths), each emission signal source is interrogated once for each different signal for every revolution of the detector carrier. Thus, in the case of a nucleic acid diagnostic assay, the contents of each receptacle is interrogated for each target analyte corresponding to the different probes employed (as indicated by different colored labels) once for each revolution of the detector carrier 230.

Figure 8:
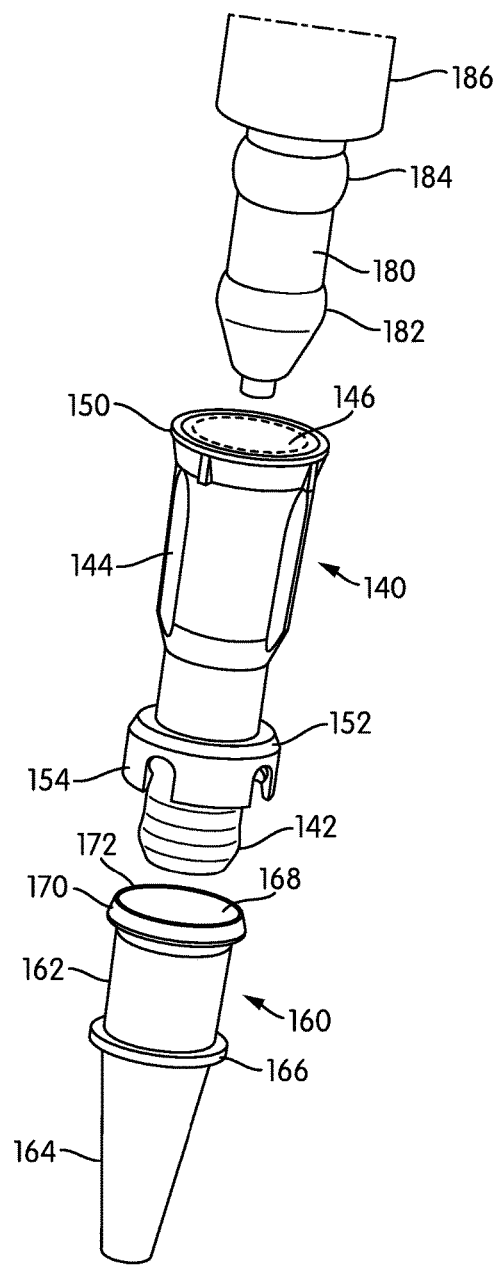
FIG. 8 is an exploded perspective view of a receptacle, a cap, and a portion of a receptacle transport mechanism configured to be inserted into the cap.
Figure 9:
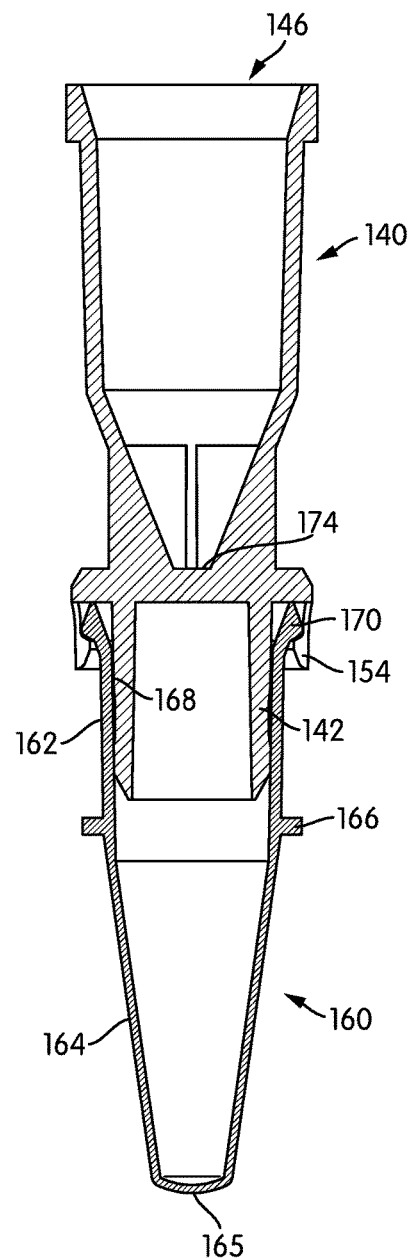
FIG. 9 is a side cross-sectional view of the cap installed in the receptacle.

Details of a receptacle (vial) 160, cap 140, and a receptacle transport mechanism 180 are shown in FIGS. 8 and 9.

As shown in FIGS. 8 and 9, an exemplary receptacle 160 is a single-piece vial that includes a body having a generally cylindrical upper portion 162 and a tapered lower portion 164. Formed on an outer surface of the body is a laterally-extending flange, which, in the illustrated embodiment, comprises an annular ring 166, which separates the upper and lower portions of the body. The upper portion 162 of the body has an open end 172 through which fluid samples are deposited into or removed from the receptacle 160. The tapered lower portion 164 has a closed end 165 that may either be flat or rounded to provide optical communication with an optical system, for example, one or more optical fibers 118 of an optical detection module.

A lip 170 circumscribes the open end 172 of the upper portion 162 and extends radially outwardly relative to a central axis of the receptacle 160. The lip 170 is configured for securable attachment to a cap 140.

The securable cap 140 includes a lower portion 142 having an outer surface configured for sealing engagement of an inner surface 168 of the receptacle 160. An upper portion 144 of the cap 140 includes an open end 146 for frictional attachment to a portion of a receptacle transport mechanism 180 (FIG. 8), such as a tubular probe of a pipettor or pick-and-place robot. Circumscribing the open end 146 of the upper portion 144 of the cap 140 is a lip 150 extending radially outward from a central axis thereof.

In various embodiments, the cap 140 is removed from the receptacle transport mechanism 180 by means of a sleeve 186 coaxially disposed over a tip 180 of the receptacle transport mechanism 180 and axially movable with respect to thereto. The sleeve 186 moves axially with respect to the tip toward a distal end of the tip and contacts the lip 150 of the cap 140, thereby pushing the cap 140 off the tip of the receptacle transport mechanism 180.

Cap 140 includes a flange 152 extending circumferentially around the cap and including a plurality of locking arms 154 that extend from the flange 152 toward the lower portion 142 of the cap 140. The locking arms 154 are shaped for securely engaging the lip 170 of the receptacle 160, and may be disposed to allow for removable attachment of the cap 140 to the receptacle 160, while maintaining a leak-proof seal of the contents thereof. The flange 152 of the cap 140 additionally serves to form a bottom 174 to separate the upper portion 144 from the lower portion 142, thereby closing the interior of the receptacle 160 from the environment when the cap 140 is inserted into a receptacle 160.

As shown in FIG. 8, the tip of a receptacle transport mechanism 180, (e.g., an automated pipettor or other pick and place apparatus) may include one or more annular ribs, as indicated at 182 and 184, for enhancing a frictional, interference fit between the tip 180 and a component into which the tip 180 is inserted, such as the cap 140 or a pipette tip (not shown).

Further details of the cap and vial are described in U.S. Patent Application Publication No. 2014-0260118, entitled "Interlocking Cap and Receptacle With Detent Feature and Method and Apparatus for Separating Interlocked Cap and Receptacle."

During operation, while multiple receptacles are being processed and one or more OMDs 240 are measuring the intensity of signal emissions from the receptacles, to the OMDs can be periodically self-checked to detect any failure or deteriorated performance. Such a failure or performance deterioration can affect the accuracy of test results, which hinge on accurate measurement of optical emissions from the contents of the receptacles. In general, such self-checking is performed by placing a reference device (e.g., a fluorescent reference device) into an operative position with respect to each OMD 240 (or in the case of a non-stationary OMD, moving the ON/D into optical communication with a reference device), measuring the optical emission intensity from the reference device, and comparing the measured intensity to an expected intensity previously established for the reference device. A difference between the measured and expected intensities that exceeds a threshold may be indicative of failure or deteriorated performance of the signal detector.

Referring again to FIGS. 5 and 6, the lid 306 may comprise a reference device as the inner surface 308 of the lid 306 may be covered with, or the entire lid may be formed from, a reference standard material, such as PEEK.

When the lid 306 configured to function as a reference device is in the closed position, the inner surface 308 faces each of the optical fibers 118. Thus, for any fibers 118 for which there is no receptacle or other optical emission source positioned thereat, the inner surface 308 of lid 306 is in an optical signal-detecting position with respect to that fiber and any OMD measuring signal through the fiber Thus, the optical emission detected or measured at that fiber will be that of the PEEK inner surface 308. By taking a monitoring reference reading through one or more of the fibers 118 with an OMD, proper performance of the OMD can be confirmed and/or the signal from the OMD can be calibrated against the known optical characteristics of the inner surface 308. In addition to confirming proper performance the OMD, a proper signal for the monitoring reference reading will confirm that the fiber is not obstructed by debris. As PEEK has been found to fluoresce across the entire spectrum of anticipated wavelengths, the inner surface can be used to calibrate or confirm operation of each OMD that is configured to detect a fluorescent signal of a different wavelength. That is, PEEK has been found to fluoresce at a repeatable wavelength and intensity depending on the wavelength and intensity of an excitation signal directed at the PEEK reference device. Thus, each OMD that is configured to detect emission signals of different wavelengths—and to excite such emissions with excitation signals of different wavelengths—can be calibrated and monitored with a single reference device constructed with a previously-characterized piece of PEEK.

In an embodiment, the lid 306 and inner surface 308 are previously characterized to determine an expected reference signal for comparison to actual signals generated by an OMD detecting a fluorescent emission from the inner surface 308.

Lid 306 is configured to cover all the signal coupling devices 114 when in the closed position, and thus all coupling devices are simultaneously exposed to the inner surface 308 or not exposed to the inner surface 308 if the lid is in the open position. Alternatively, each of a plurality of lids configured as reference devices may be configured to cover one or more, but less than all, signal coupling devices 114 when the lid is in a closed position. Thus, certain lids may be selectively closed to cover certain signal coupling devices—or to cover a cap 140 and receptacle 160 disposed over the signal coupling device(s) 114.

As noted, the reference device may be configured as a component—or in the shape of a component—that is used in conjunction with the OMD. Such reference devices are formed from a suitable optical reference standard material, such as PEEK. As shown in FIGS. 10-15, such a reference device may be embodied in a reference "vial" formed completely or partially from PEEK and configured to be connectable to a cap, such as cap 140 described above, and placed into an operative, signal-detecting position with respect to the OMD or with respect to a fiber coupled to the OMD in the same manner that a receptacle 160 coupled to the cap 140 is placed into an operative, signal-detecting position.

FIGS. 10-12 show a first embodiment of such a reference vial 316. Note that the term "vial" is merely intended to reflect that the vial 316 has a configuration similar to the receptacle vial 160 described above, but a reference vial, such as reference vial 316, may not be configured to hold liquid or other substance. The reference vial 316 includes a lower body 328 and an upper body 318. In the illustrated embodiment, the lower body 328 comprises a tapered section 330 terminating at a blunt end 332. The upper body 318 may include a collar 326 partially or completely surrounding the upper body 318. A blind recess 320 is formed in the upper body 318 and is configured to receive a lower portion 142 of a cap 140. A peripheral lip 324 surrounds the recess 320 and a tapered opening 322 facilitates the insertion of the lower portion 142 of the cap 140 into the recess 320, where the lower portion 142 frictionally engages an inner surface of the recess 320.

After being secured to a cap 140, e.g., when the locking arms 154 snap over the lip 324 of the reference vial 316, the reference vial 316 may be moved by a receptacle transport mechanism and placed in an operative position with respect to an OMD or with respect to an optical fiber that is in optical communication with the OMD. In an exemplary embodiment, as shown in FIG. 5, the reference vial 316 may be placed above any of the signal coupling devices 114 within a compartment 305 of the lid assembly 300. The lower body 328 of the reference vial 316 may be tapered as shown at 330 to facilitate insertion of the reference vial 316 into a receptacle holding structure, with the vial 316 supported by the collar 326 above the signal couple element 114.

When excited by an excitation signal emitted by an OMD and transported through the optical fiber 118, the reference vial 316 will fluoresce at a predetermined intensity. The reference vial 316 will be supported in an operative position with respect to the signal coupling device 114 so that an excitation signal emitted through the signal coupling device 114 will impinge upon a portion of the vial 316 (such as the blunt end 332) and a portion of the emission fluorescence from the reference vial 316 will impinge upon the signal coupling device 114.

The geometry of the receptacle vial 316 may be altered to vary the emission signal emitted by the vial 316. For example, the length of the lower portion 328 may be varied to vary the distance between the blunt end 332 of the vial 316 and the fiber 318 or signal coupling device 114. The closer the blunt end 332 of the vial is to the coupling device 114, the stronger the emission signal (i.e., the greater the intensity) that will be received by the fiber 118 and thus by the MID. Thus, reference vials of varying lengths, for example short, medium, and long, can be prepared for generating reference emissions of increasing intensity. Each differently sized reference vial 316 can itself be calibrated with respect to a standard OMD, the expected emission signal generated by that vial can be recorded, and the vial can then be used to calibrate the signals generated by other, uncalibrated OMDs. In addition, the width or diameter of the lower portion 328, for example, the diameter of the blunt end 332, can be varied so as to alter the reference emission generated by the vial 316.

In an embodiment, the reference vial 316 is previously characterized to determine an expected reference signal for comparison to actual signals generated by an OMD detecting a fluorescent emission from the vial 316.

Figure 15:
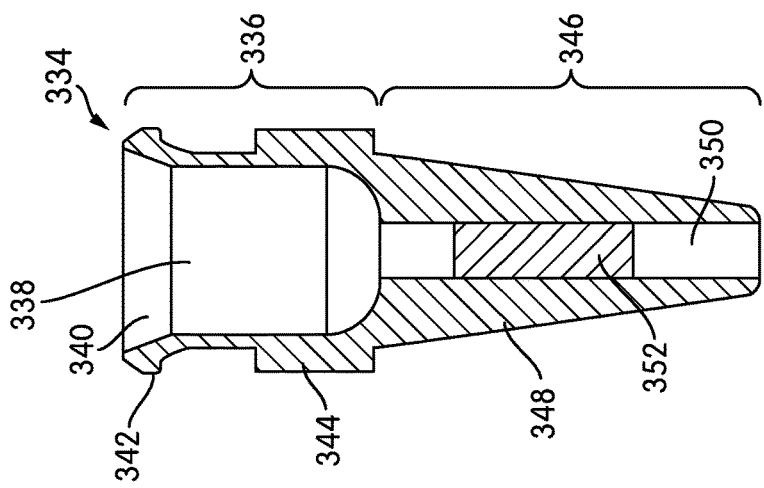
FIG. 15 is a cross-sectional view of the alternate optical reference vial along the line 15-15 in FIG. 14.
Figure 14:
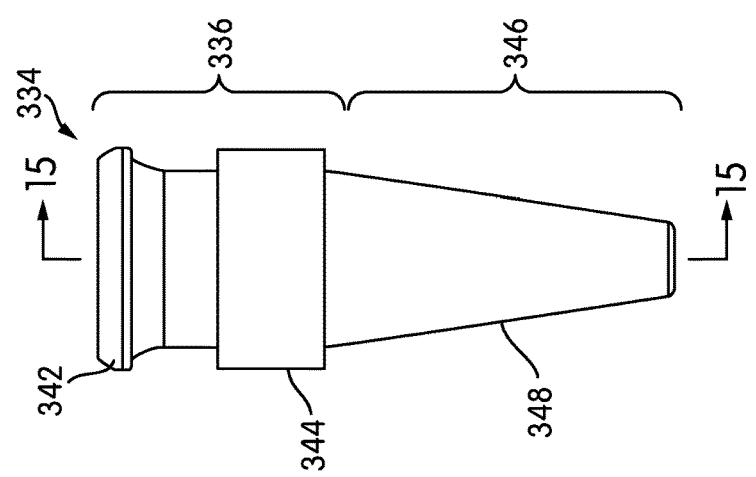
FIG. 14 is a side view of the alternate optical reference vial.
Figure 13:
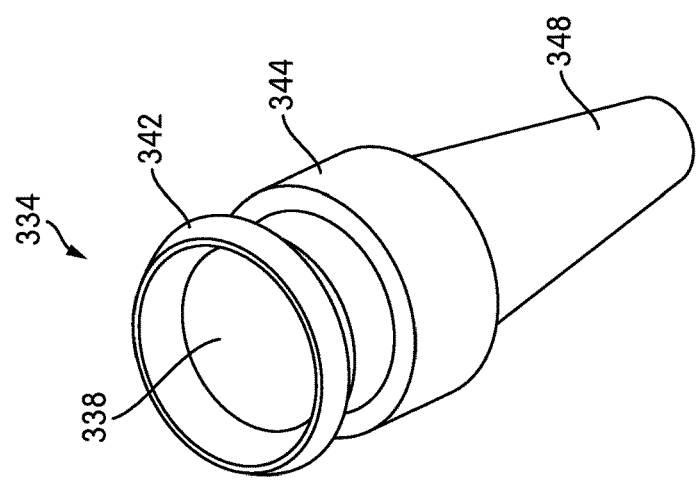
FIG. 13 is a perspective view of an alternate optical reference standard vial.

FIGS. 13-15 show a second embodiment of a reference vial 334. As with reference vial 316, reference vial 334 may not be configured to actually contain a liquid or other substance. The vial 334 includes a lower body 346 and an upper body 336. In the illustrated embodiment, the lower body 346 comprises a tapered section 348. The upper body 336 includes a collar 344 partially or completely surrounding the upper body 336. A blind recess 338 is formed in the upper body 336 and is configured to receive a lower portion 142 of a cap 140. A peripheral lip 342 surrounds the recess 338 and a tapered opening 340 facilitates the insertion of the lower portion 142 of the cap 140 into the recess 338, where the lower portion 142 frictionally engages an inner surface of the recess 338.

Reference vial 334 may be made from a non-fluorescing material, such as Delrin®, and includes a channel 350 extending through all or part of the lower portion 346. A piece of reference standard material, such as a reference plug 352 made from PEEK, can be inserted into the channel 350. After being secured to a cap 140, e.g., when the locking arms 154 snap over the lip 342 of the reference vial 334, the reference vial 334 may be moved by a receptacle transport mechanism and placed in an operative position with respect to an OMD or with respect to an optical fiber that is in optical communication with the OMD. In an exemplary embodiment, as shown in FIG. 5, the reference vial 334 may be placed above any of the signal coupling devices 114 within a compartment 305 of the lid assembly 300. The lower body 346 of the reference vial 334 may be tapered as shown at 348 to facilitate insertion of the reference vial 334 into a receptacle holding structure, with the vial 334 supported by the collar 344 above the signal couple element 114.

When excited by an excitation signal emitted by an OMD and transported through the optical fiber 118, the reference plug 352 will fluoresce at a predetermined intensity. The reference vial 334 will be supported in an operative position with respect to the signal coupling device 114 so that an excitation signal emitted through the signal coupling device 114 will impinge upon the reference plug 352 and a portion of the emission fluorescence from the reference vial 334 will impinge upon the signal coupling device 114.

To alter the geometry of the reference vial 334 to vary an emission signal, the position of the reference standard plug 352 within the channel 350 can be varied, such as by moving it upwardly to move it away from the signal coupling device 114 and fiber 118 (to thereby diminish the reference emission received by fiber 118, and thus by the OMD), or by moving it downwardly to move it closer to the coupling device 114 and fiber 118 (to thereby strengthen the reference emission received by fiber 118, and thus by the OMD). In addition, the diameter of the plug 352 can be varied to further alter the emission reference signal generated by the reference vial 334—a larger diameter plug will emit a larger reference emission and a smaller diameter plug will emit a smaller reference emission.

The reference vial 334 and reference standard plug 352 may be previously characterized to determine an expected reference signal for comparison to actual signals generated by an OMD detecting a fluorescent emission from the reference vial 334.

Figure 18:
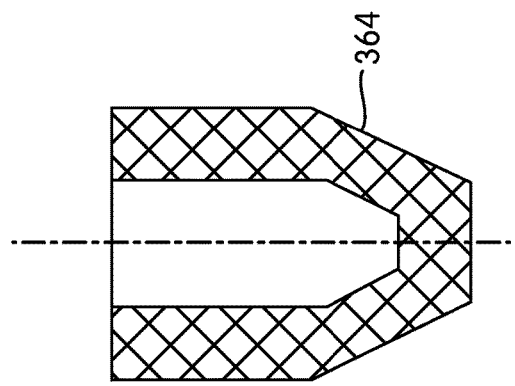
FIGS. 17 and 18 are side cross-sectional views of exemplary optical reference caps configured to be secured to an end of the receptacle transport mechanism.
Figure 17:
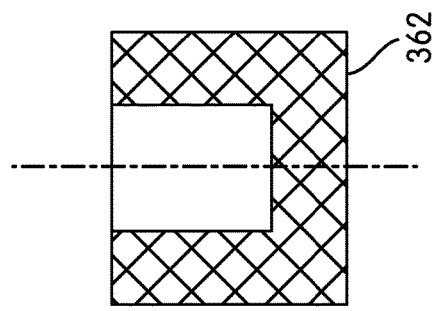
Figure 16:
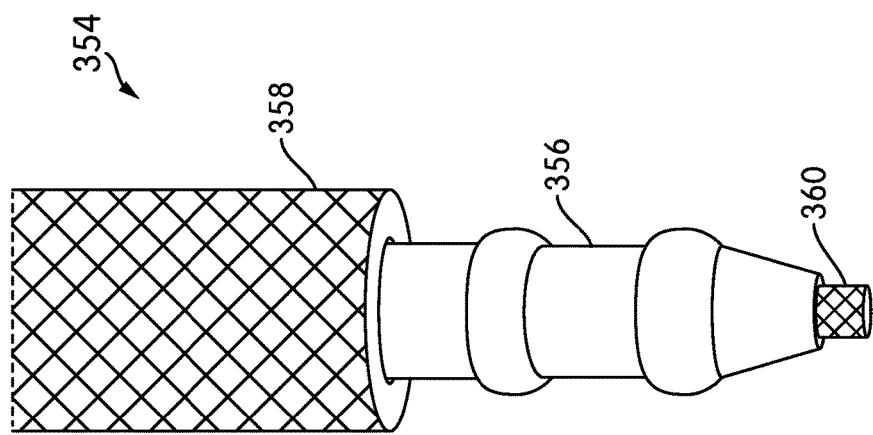
FIG. 16 is a perspective view of a portion of a receptacle transport mechanism including portions formed from optical reference standard material.

A further alternative for providing a reference device is illustrated in FIGS. 16-18. As shown in FIG. 16, a reference device may be embodied in one or more portions on an automated pipettor or receptacle transport mechanism 354. For example, a tip 360 in the form of a dowel made from an optical reference material such as PEEK can be inserted into an end of the tip 356. Alternatively, or in addition, the strip sleeve 358, or at least a terminal end of the strip sleeve 358, can be made from an optical reference material such as PEEK. The apparatus 354 can be placed into an operative position with respect to an OMD or with respect to a fiber coupled to an OMD and a reference emission generated by the tip 360 when subjected to an excitation signal can be used to calibrate the OMD or to monitor the performance of the OMD. Similarly, the strip sleeve 358 can be moved axially with respect to the tip 356 so that the terminal end of the sleeve 358 extends below the tip 356 and the end of the strip sleeve 358 can be used to generate a reference emission when the apparatus 354 is placed into an operative position with respect to an OMD or fiber and is subjected to an excitation signal.

The tip 360 and sleeve 358 may be previously characterized to determine an expected reference signal for comparison to actual signals generated by an OMD detecting a fluorescent emission from the tip 360 or sleeve 358.

In addition, or alternatively, reference devices may comprise tools made from PEEK and configured to be securable to the end of the receptacle transport mechanism 354. For example, as shown in FIGS. 17 and 18, a blunt end reference cap 362 or a conical end reference cap 364 can be provided to fit frictionally onto the tip 356 of the receptacle transport mechanism 354. The receptacle transport mechanism 354 can then be used to place the reference cap 362, 364 into an operative position with respect to an OMD or with respect to a optic fiber coupled to the OMD so that a signal generated by the cap 362, 364 when exposed to an excitation signal can be detected by an OMD. Again, as described above, the geometry of the reference cap can be varied to alter the reference emission generated thereby. For example, by making the cap long or short, blunt or pointed or by varying the width of the cap, the reference emission can be altered and customized.

The caps 362, 364 may be previously characterized to determine an expected reference signal for comparison to actual signals generated by an OMD detecting a fluorescent emission from the caps 362, 364.

A reference device, such as reference vials 316, 334, pipettor or receptacle transport mechanism 354 having portions formed from a reference material such as PEEK, or caps 362, 364, can be used to ensure the proper installation of optic fibers in a fiber reformatter, such as the reformatters, e.g., 102, 120, shown in FIGS. 1-3 and 5. As shown in the table of FIG. 4, there is a specific required mapping between fiber-positioning holes 110, 126 in the base 108, 126 and the optical coupling elements 114, 132 in the interface plate 112, 130 (i.e., between the first and second ends of the fibers). Since the positions of the receptacles 160 on the interface plate will be known, it is necessary that each fiber corresponds to the correct receptacle location so that the signal measured at each fiber can be associated with the correct receptacle 160. Proper positioning of the fibers can be confirmed by placing a reference device at each receptacle location, one at a time, and measuring the emission signal at the fiber that should correspond to that location. If a proper reference signal is detected, this confirms that the fiber is properly installed. If no signal is detected, this is an indication that the fibers have been crossed.

For multiple point calibration—i.e., calibrating to multiple, e.g., 2, 3, 4, etc., different reference emission intensities, reference devices of different geometries (e.g., different sizes) can be used to generate the different reference emission intensities. Alternatively, calibration could be performed by some combination of reference devices comprising components configured to be used in conjunction with the OMD as well as structural components of the OMD or instrument in which the OMD is incorporated. For example, calibration could be performed using a combination of reference vials 316, 334, pipettor or receptacle transport mechanism 354 having portions formed from a reference material such as PEEK, and/or caps 362, 364 along with a lid 306 having an inner surface 308 made from PEEK or similar material.

Calibration of fluorometers, or other OMDs, can be performed using a "master reference device" made from PEEK to standardize the fluorometer to the expected fluorescent emission of the master reference device. In this context, the "master reference device" may comprise a plate or panel that can be placed in an operative, signal-detecting position with respect to the fluorometer and which may comprise a part of a lid structure or other structural element of an instrument. Alternatively, the master plate could be a tool, such as a vial, a pipettor, a receptacle transport mechanism, or a cap for a pipettor or receptacle transport mechanism. The "master reference device" is characterized by a standard fluorometer—i.e., a fluorometer known to be properly calibrated and functioning properly—to identify an expected reference emission signal from the master reference device that is recorded for the master reference device. A second master reference device may be characterized by the standard fluorometer and the expected reference emission signal for the second master reference device can be determined and recorded. To ensure that the standard fluorometer remains "calibrated" the standard fluorometer may be kept out of operational use and may be dedicated solely to characterizing master reference devices.

To calibrate a fluorometer using a master reference device, an emission reading of the master reference device is taken with the fluorometer and that reading is compared to the reference emission reading recorded for the master reference device. If the actual and expected readings agree to within a predetermined threshold, an emission reading of the second master reference device may be taken with the fluorometer and that reading compared to a reference emission reading recorded for the second master reference device. If the actual and expected readings for the second master reference device agree to within the predetermined threshold, the fluorometer may be deemed "calibrated" or "standardized." In other embodiments, the fluorometer calibration may be confirmed using only one or more than two, e.g., 3, 4, or more, master reference devices.

Alternatively, if the actual and expected readings for the first master reference device do not agree to within the predetermined threshold, the output signal of the fluorometer may be adjusted, for example, by adjusting gains in the signal processing electronics, until the actual and expected readings do agree to within the predetermined threshold. The output of the fluorometer may be confirmed with a reading of the second master reference ((and, optionally, third, fourth, etc. master reference devices).

Periodically, during the operational life of the fluorometer, it may be checked against the master reference device. If the actual and expected readings agree, the fluorometer may be deemed to be still calibrated and operating properly. The fluorometer may be confirmed with one or more additional master reference devices.

If the actual and expected readings do not agree, the fluorometer may be checked again with the second master reference device.

If there is ever any doubt as to whether the reference emissions of the master reference devices have changed, for example if the actual and expected readings do not agree for the first master reference device, but do agree for the second master reference device (or vice versa), the master reference devices can be checked again using the standard fluorometer to re-characterize the master reference device or to determine if the master reference device should be replaced.

While the present disclosure has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the disclosures require features or combinations of features other than those expressly recited in the claims. Accordingly, the present invention is deemed to include all modifications and variations encompassed within the spirit and scope of the following appended claims.

The invention claimed is:

1. An optical signal detection module comprising:
a first optical measurement device configured to detect a first optical emission signal comprising a first wavelength emitted from at least one first optical emission source;
a second optical measurement device configured to detect a second optical emission signal including a second wavelength emitted from at least one second optical emission source, the second wavelength being different than the first wavelength; and
a cover element moveable between (i) closed position covering the at least one first optical emission source and the at least one second emission source and (ii) an open position not covering the at least one optical emission source and the at least one second emission source, the cover element including an inner surface comprising a material that emits a stable and repeatable reference emission comprising the first wavelength and the second wavelength,
wherein the first optical measurement device, the second optical measurement device, and the cover element are configured so that when the cover element is in the closed position, the inner surface is in a signal-detecting position of each of the first optical measurement device and the second optical measurement device so that each of the first optical measurement device and the second optical measurement device is exposed to the reference emission.

2. The optical signal detection module of claim 1, wherein the inner surface of the cover element comprises a thermoplastic from the polyaryletherketone (PAEK) family of semi-crystalline thermoplastics.

3. The optical signal detection module of claim 1, wherein the inner surface of the cover element comprises polyether ether ketone (PEEK).

4. The optical signal detection module of claim 1, wherein each of the first optical measurement device and the second optical measurement device comprises at least one fluorometer.

5. The optical signal detection module of claim 1, further comprising a drive assembly coupled to the cover element and configured to move the cover element between the open position and the closed position.

6. The optical signal detection module of claim 1, further comprising a holding structure configured to hold the at least one first optical emission source in the signal-detecting position with respect to the first optical measurement device and configured to hold the at least one second optical emission source in the signal-detecting position with respect to the second optical measurement device, wherein the cover element covers and limits access to the holding structure when the cover element is in the closed position.

7. The optical signal detection module of claim 6, further comprising at least one first optical fiber that transmits the reference emission from the inner surface of the cover element to the first optical measurement device and at least one second optical fiber that transmits the reference emission from the inner surface of the cover element to the second optical measurement device.

8. The optical signal detection module of claim 6, wherein the at least one first optical emission source comprises at least one first receptacle containing a first substance that emits a first optical signal, and the holding structure comprises at least one first receptacle holding structure configured to hold the at least one first receptacle in the signal-detecting position with respect to the first optical measurement device; and
wherein the at least one second optical emission source comprises at least one second receptacle containing a second substance that emits a second optical signal, and the holding structure further comprises at least one second receptacle holding structure configured to hold the at least one second receptacle in the signal-detecting position with respect to the second optical measurement device.

9. The optical signal detection module of claim 8, further comprising a robotic arm configured to move the at least one first receptacle into and out of the at least one first receptacle holding structure and configured to move the at least one second receptacle into and out of the at least one second receptacle holding structure.

10. The optical signal detection module of claim 9, wherein the at least one first optical emission source further comprises at least one first cap coupled to the at least one first receptacle, thereby closing the at least one first receptacle; and
wherein the at least one second optical emission source further comprises at least one second cap coupled to the at least one second receptacle, thereby closing the at least one second receptacle.

11. The optical signal detection module of claim 10, wherein the robotic arm is configured to couple with the at least one first cap and configured to couple with the at least one second cap.

12. The optical signal detection module of claim 11, wherein the robotic arm comprises a tubular portion configured for frictional engagement with a portion of the at least one first cap and with a portion of the at least one second cap.

13. The optical signal detection module of claim 9, wherein the robotic arm comprises a pipettor.

14. The optical signal detection module of claim 9, wherein the robotic arm comprises a pick-and-place robot.

* * * * *